United States Patent [19]
Futagawa et al.

[11] Patent Number: 5,865,309
[45] Date of Patent: Feb. 2, 1999

[54] DUAL-CHAMBERED CONTAINER AND METHOD OF MAKING SAME

[75] Inventors: Hitoshi Futagawa; Noriyoshi Yamamoto, both of Kusatsu, Japan

[73] Assignee: Nissho Corporation, Osaka, Japan

[21] Appl. No.: 959,278

[22] Filed: Oct. 24, 1997

Related U.S. Application Data

[63] Continuation of Ser. No. 613,696, Mar. 11, 1996, abandoned.

[30] Foreign Application Priority Data

Mar. 23, 1995 [JP] Japan .................................... 7-063740

[51] Int. Cl.$^6$ .................................................. B65D 25/08
[52] U.S. Cl. ............................................ 206/219; 424/400
[58] Field of Search ................................. 424/400, 443

[56] References Cited

U.S. PATENT DOCUMENTS

| | | | |
|---|---|---|---|
| 3,608,709 | 9/1971 | Pike ............................................. | 206/47 |
| 3,679,509 | 7/1972 | Fielibert ..................................... | 156/182 |
| 3,983,994 | 10/1976 | Wyslotsky ................................. | 206/219 |
| 4,608,043 | 8/1986 | Larkin ........................................ | 604/87 |
| 5,423,421 | 6/1995 | Inoue et al. .............................. | 206/219 |
| 5,616,337 | 4/1997 | Kasianovitz et al. ..................... | 424/414 |

*Primary Examiner*—Gollamudi S. Kishore
*Assistant Examiner*—Kathryne E. Shelborne
*Attorney, Agent, or Firm*—Kubovcik & Kubovcik

[57] ABSTRACT

A dual-chambered container includes a chamber which contains, for example, a dry drug and a chamber which contains, for example, a medical liquid. The chambers are defined in first and second bags, with each bag having a weak seal formed in a side thereof. The bags are formed separately and then joined to one another so that the weak seals therein are positioned so that a passageway is formed between the bags when the weak seals are forcibly broken. The chambers can be sterilized independently of each other and, consequently, the container can be manufactured in a manner which minimizes the amount of labor required.

5 Claims, 4 Drawing Sheets

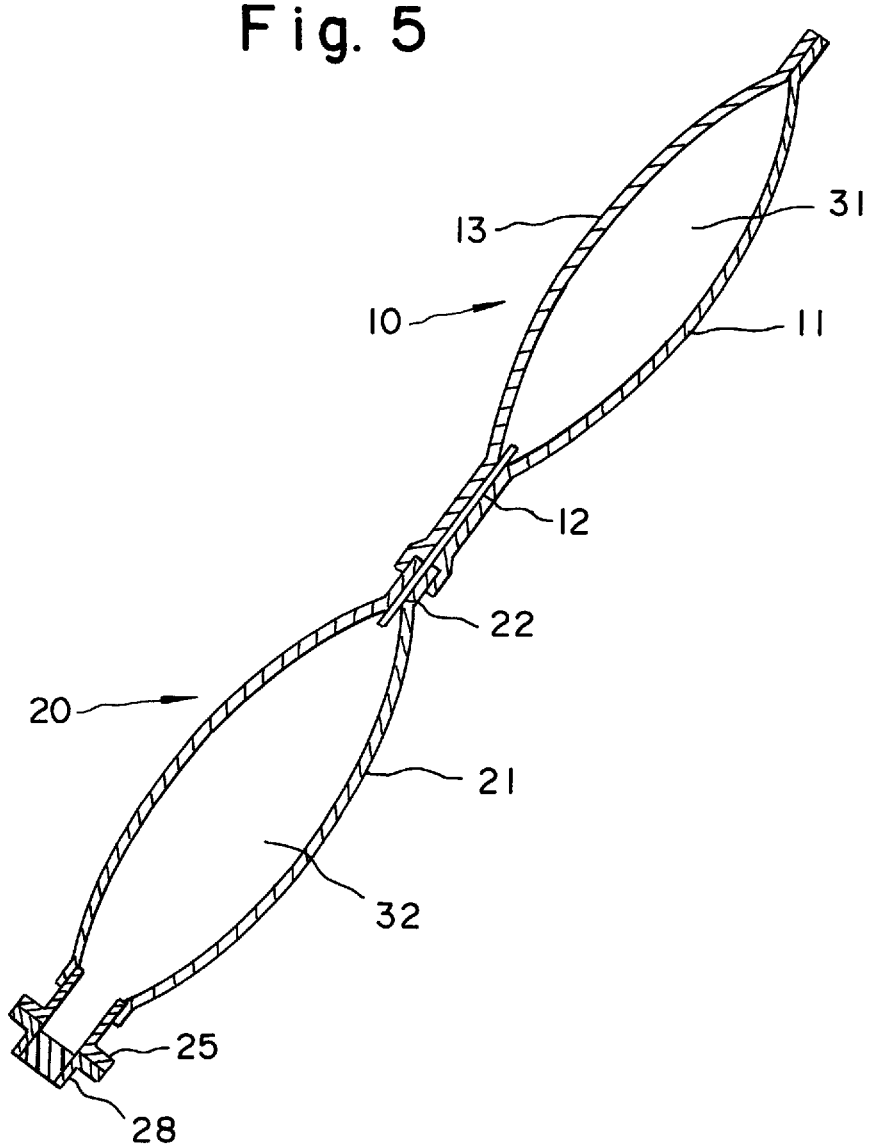

DUAL-CHAMBERED CONTAINER AND METHOD OF MAKING SAME

This application is a continuation of application Ser. No. 08/613,696, filed Mar. 11, 1996, now abandoned.

BACKGROUND OF THE INVENTION

1. Field of the Invention

The present invention relates to a dual-chambered container and a method of making the container. The dual-chambered container is designed to hold a medical liquid and a dry medical material in separate chambers so that the liquid and the dry material can be intermixed on demand.

2. Prior Art

Conventional dual-chambered containers for medical uses are flexible and have a partition dividing the interior of the container into chambers. The chambers of the container are brought into fluid communication with each other by breaking the partitions. One disadvantage of these containers is that small amounts of water and/or gases can permeate through the partitions, which are made of a synthetic resin. In the case where a hygroscopic and unstable drug such as an antibiotic is held in one chamber and a solvent or diluent is held in the other chamber, even very small "interchamber" permeations of water or gases are problematic. Further, an amino acid solution such as a tryptophan solution is so susceptible to oxidation that interchamber permeation can cause problems when such solution and a sucrose or protein solution are accommodated in the same container. Thus, an effective countermeasure for preventing water or oxygen gas from penetrating the partition and affecting the drug has been needed (as proposed, for example, in Japanese Patent Publication No. 63-20550). In one proposal, an external bag accommodating the drug and the liquid together with a desiccant or deoxidant is made of an impermeable material that intercepts water and oxygen gas. The desiccant, however, absorbs water from the liquid so that the hygroscopic drug cannot be dehydrated, with the liquid being condensed to an undesirable extent. In another proposal intended to resolve this drawback, the chamber for receiving the hygroscopic or readily oxidizing drug is covered with an external wall through which water and oxygen cannot permeate. The desiccant and/or deoxidant are sandwiched between the external wall and the chamber wall (as disclosed in Japanese Unexamined Patent Publication Nos. 4-364850, 4-364851, and 6-14975).

In each prior art container the chambers for receiving the drug and the liquid, respectively, are formed integral with each other. The liquid is poured in one chamber, which is then sealed with a plug and sterilized. Subsequently, the drug is placed in the other chamber, which is then sealed and wrapped with a cover. Disadvantages inherent in these prior art containers are: (i) the chamber for the drug and the chamber for the liquid cannot be sterilized separately; (ii) both chambers, one of which is already filled with the liquid, must be sterilized and dried as a whole at first, before the sealed portion of one chamber is opened again to receive the drug in an aseptic manner, thus requiring additional labor; and (iii) during steam sterilization, the interior of the drug-receiving chamber is not exposed to vapor and, consequently, is unlikely to be sterilized sufficiently.

SUMMARY OF THE INVENTION

An object of the present invention is therefore to resolve those drawbacks inherent in the prior art and, more particularly, to provide a novel dual-chambered container having chambers that can be sterilized separately. An additional object is to provide a method of manufacturing a dual-chambered container which reduces the amount of labor required to manufacture such a container.

In a first aspect, the present invention provides a dual-chambered container including a first bag having a chamber therein and a second bag having a chamber therein. In a preferred embodiment, the chamber in the first bag contains a dry drug and the chamber in the second bag contains a medical liquid. The first and second bags have weak seals in one of their sides. The bags are joined by, for example, fusion bonding so that the weak seals in the bags are positioned so that a passageway is formed between the bags when the weak seals are forcibly broken.

In a preferred embodiment, the first and second bags are formed and joined to one another as follows. The weak seal in the first bag is formed by sandwiching a weak sealing member between two main plastic sheets and fusion bonding the member to the plastic sheets so that portions of the sheets form ears that are not bonded to one another but instead are left free at one end of the first bag. The weak seal in the second bag is formed by fusion bonding a weak-sealing member in a cylindrical plastic sheet so that an end portion of the member protrudes from an end of the second bag to form a tongue. This tongue of the second bag is inserted in and between the free ears of the first bag so that outer ends of the weak-sealing members in each bag are located in juxtaposition. The ears of the first bag are fusion bonded to the weak-sealing members of each bag and to the end of the second bag in which the weak-sealing member is disposed.

Preferably, each weak-sealing member is a small sheet piece made of a polymer blend or mixture of at least two polymers, one of which constitutes the bag body and has a limited affinity to the other polymer or polymers included in the blend or mixture.

In a second aspect, the present invention provides a method of making the dual-chambered container. The method includes the steps of forming a first bag having a weak seal in a side thereof, forming a second having a weak seal in a side thereof, and fusion bonding the sides of the bags so that the weak seals therein are positioned so that a passageway is formed between the bags when the weak seals are forcibly broken. Thus, when the weak seals in each bag are forcibly broken, the bags are in fluid communication.

As described above, in a preferred embodiment the first bag contains a dry drug and the second bag contains a medical liquid to be mixed with the drug on demand. In use, the weak seals isolating the interior of the first bag from that of the second bag can be readily broken by compressing the weak seal in the second bag with one's hand. Thus, the interiors of the bags will be put into fluid communication to intermix the drug and the liquid. One of the significant advantages of the dual-chambered container of the invention is that the first and second bags are prepared separately, before being joined together, so that each bag can be sterilized by itself. In particular, the first bag, which contains a dry drug in the preferred embodiment, can be thoroughly disinfected.

The separate preparation of the first bag and the second bag is particularly advantageous in that sterilization of these bags can be done in different manners. In the case where a dry drug is placed in the first bag, any method other than steam sterilization can be employed to disinfect the first bag. Therefore, the four sides of the first bag need not be sealed to keep water vapor out of its interior. In the case where the second bag is correspondingly filled with a medical liquid, the second bag can be subjected to steam sterilization and dried. The weak seal of the thus inflated second bag need not be severed when the second bag is connected to the first bag. Thus, the container as a whole can quickly accommodate the dry drug without requiring much time or labor.

BRIEF DESCRIPTION OF THE DRAWINGS

FIG. 5 is a perspective view of a dual-chambered container shown on an enlarged scale and including the first and second bags that have been prepared and connected to one another.

DETAILED DESCRIPTION OF THE PREFERRED EMBODIMENTS

Figure 1A:
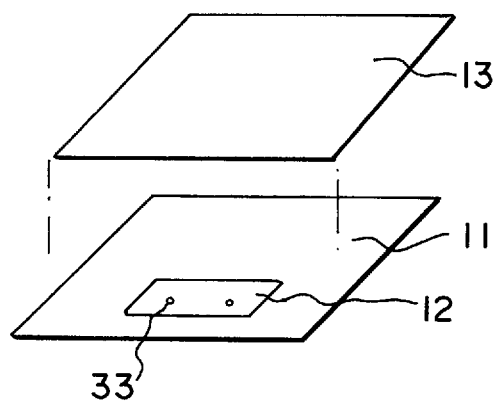
FIGS. 1A to 1D show the sequential steps of preparing the first bag of the dual-chambered container of the invention.

Preferred embodiments of the present invention will now be described with reference to the accompanying drawings.

The method described herein to produce a dual-chambered container includes, for defining a first chamber, forming a first bag 10 having weak seal 19 in a side thereof. For defining a second chamber, a second bag 20 having weak seal 29 in a side thereof is formed. Weak seals 19 and 29 are formed by weak-sealing members, as will be described in detail below. The method also includes the step of fusion bonding the sides of the first and second bags so that weak seals 19 and 29 are positioned so that a passageway is formed between the first and second bags when weak seals 19 and 29 are forcibly broken.

Figure 1B:
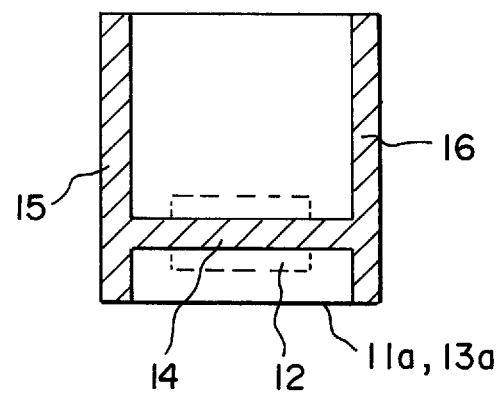
Figure 1C:
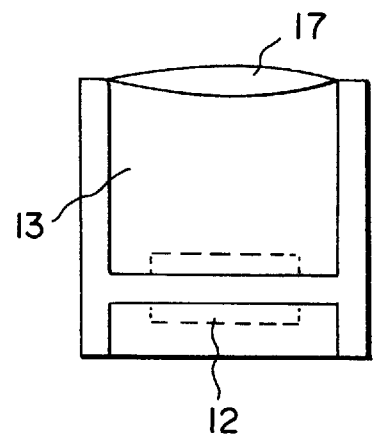
Figure 1D:
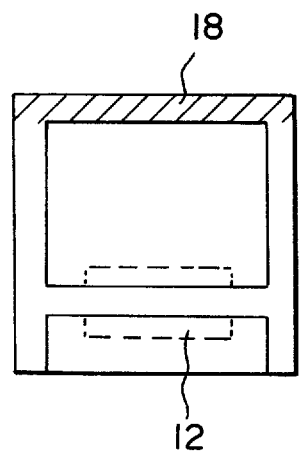

In a preferred embodiment, first bag 10 receives a dry drug. The preferred steps for manufacturing first bag 10 are shown in FIGS. 1A to 1D. First, rear main sheet 11, frontal main sheet 13, and small sheet piece 12, which serves as the weak-sealing member, are prepared. As can be seen in FIG. 1A, sheet piece 12 is placed between main sheets 11 and 13. Sheet piece 12 is thus embedded between main sheets 11 and 13 at a predetermined distance from one of the overlapping sides of the main sheets. If desired, sheet piece 12 may be secured to main sheet 11 by point welds 33. Next, overlapping sides 15 and 16 of the main sheets are fusion bonded to one another. Strip 14 extending between sides 15 and 16 and across small sheet piece 12 is also fusion bonded to thereby provide a bag-shaped article as shown in FIG. 1B. Thus, weak seal 19 (see FIG. 3) includes the portion of sheet piece 12 bonded to main sheets 11 and 13, as well as ears 11a and 13a located outside of fusion-bonded strip 14 (see FIG. 1B and FIG. 3). In the preferred embodiment, bag 10 is then sterilized using radiation or ethylene oxide gas (EOG), before the drug (not shown) is put through mouth 17 (see FIG. 1C) into the bag. The lips are then fusion bonded at 18 to close the mouth (see FIG. 1D).

Rear sheet 11 may be an aluminum foil laminate such as "PET/aluminum foil/PE," composed of an outer layer of polyethylene terephthalate (PET), an inner layer of polyethylene (PE), with the foil interposed therebetween. An additional layer may intervene between the foil and the inner PE layer. Frontal sheet 13 may be a laminate of PET film having its faces coated with an evaporated-and-deposited silica (SiO$_2$) layer, such as "(PE+PP)/SiO$_2$/PET/SiO$_2$/PE." The outer layer of this laminate is composed of a copolymer of ethylene and propylene or, alternatively, composed of a polyethylene layer, with the inner layer being a polyethylene film. Small sheet piece 12 serves as the weak-sealing member and, consequently, must be made of a resin that can be fusion bonded at a moderately low bonding strength to the inner polyethylene layers of main sheets 11 and 13. By way of example, a preferred weakly-bonding resin is a polymer blend composed of polyethylene and polypropylene having a limited affinity to polyethylene. The ratio by weight of polyethylene to polypropylene in the blend is preferably 3:7 to 7:3.

Figure 2A:
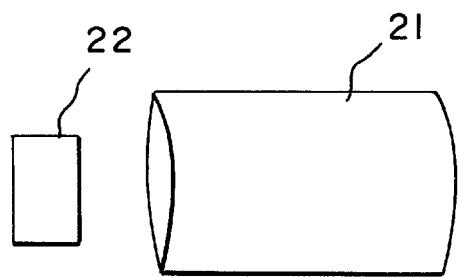
FIGS. 2A to 2F show the sequential steps of preparing the second bag of the dual-chambered container of the invention.
Figure 2B:
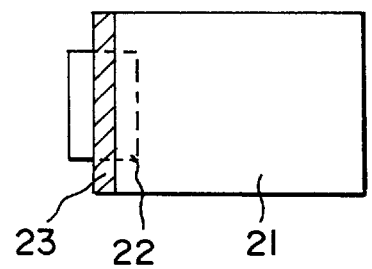
Figure 2C:
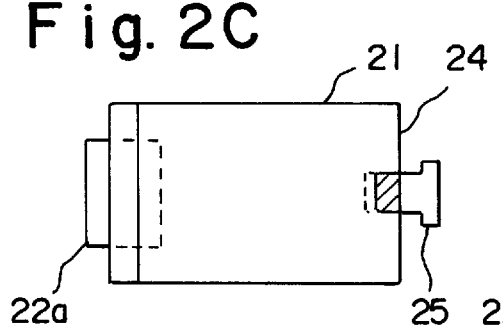
Figure 2D:
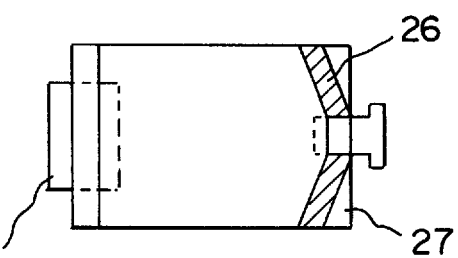
Figure 2E:
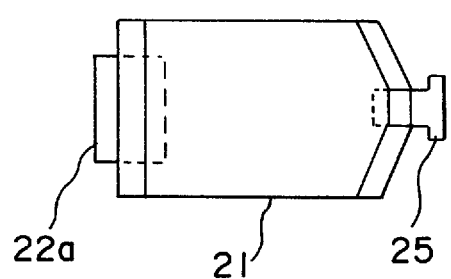
Figure 2F:
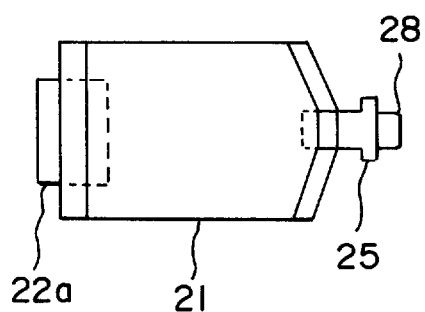

In a preferred embodiment, second bag 20 receives a medical liquid. The preferred steps for manufacturing second bag 20 are shown in FIGS. 2A to 2F. First, cylindrical sheet 21 and small sheet piece 22, which serves as a weak-sealing member, are prepared as shown in FIG. 2A. Cylindrical sheet 21 may be formed of the same polyethylene resin as that which forms the inner layer of first bag 10. Those skilled in the art will recognize that sheet 21 also may be formed by a pair of rectangular sheets having opposing edges bonded to one another. Sheet piece 22 is then placed in an opening at one end of cylindrical sheet 21 so that sheet piece 22 protrudes outwardly a predetermined distance from the opening. Next, the lips defining the opening are fusion bonded to each other at 23 and to sheet piece 22 to thereby provide a bag-shaped article as shown in FIG. 2B. Thus, weak seal 29 (see FIG. 3) includes the portion of sheet piece 22 bonded to cylindrical sheet 21, as well as tongue 22a, i.e., the portion of sheet piece 22 protruding from sheet 21. As shown in FIG. 2C, a port 25 is fusion bonded to end opening 24 of second bag 20. Front and rear shoulders 26 located beside port 25 are also fusion bonded to one another (see FIG. 2D). Second bag 20 is finished by removing flashes 27 as seen in FIG. 2E. A medical liquid (not shown) can then be supplied into the second bag through port 25, which is subsequently stopped with plug 28 (see FIG. 2F).

In the preferred embodiment, second bag 20 inflated with the liquid and stopped with plug 28 fitting in port 25 is then exposed to high pressure steam for the purpose of sterilization. Cylindrical sheet 21 may be made of polyethylene or polypropylene, with sheet piece 22, i.e., the weak-sealing member, being made of the same material from which sheet piece 12 in first bag 10 is made. Tongue 22a, i.e., the protruding portion of sheet piece 22 in second bag 20, should be shorter than ears 11a and 13a of first bag 10. Ears 11a and 13a, as well as tongue 12a, i.e., the portion of sheet piece 12 that extends outside strip 14, are not yet fusion bonded to any other member. Because ears 11a and 13a are longer than tongue 22a, ears 11a and 13a can overlap with longitudinal end 23 of cylindrical sheet 21. Thus, when ears 11a and 13a of the first bag 10 are fusion bonded to end 23 of second bag 20 outward leakage of medical liquid is prevented when the weak-sealing members are disjoined from the remaining bag portions surrounding them.

Figure 3:
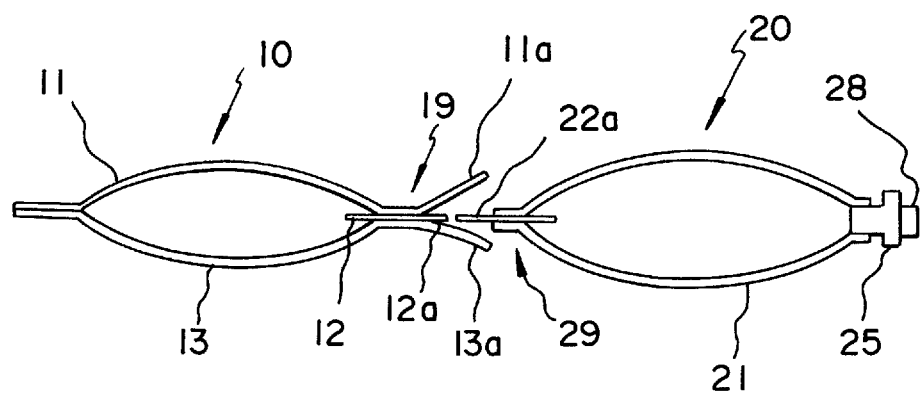
FIG. 3 is a side elevation showing the first step of connecting the first bag to the second bag.
Figure 4:
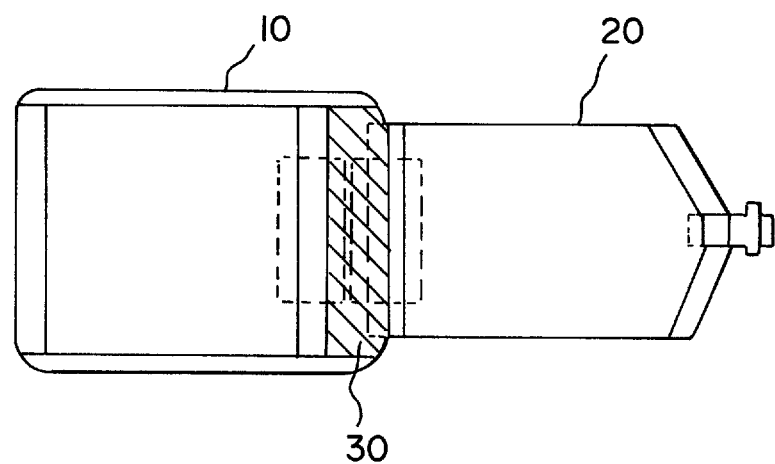
FIG. 4 is a plan view showing the first and second bags in the subsequent step of connecting them together.

In the preferred embodiment, first bag 10 is then fixedly secured to second bag 20 in the following manner. First, bags 10 and 20 are set in position as shown in FIG. 3. Weak seal 29 of second bag 20 is put in and between ears 11a and 13a of the corresponding weak seal 19 of first bag 10. Then ears 11a and 13a are rigidly fusion bonded to one another and also to the portion of cylindrical sheet 21 forming weak seal 29, thereby forming a rigid weak seal 30 extending between the first and second weak seals 19 and 29, respectively. Ears 11a and 13a of first bag 10, however, are weakly fusion bonded to tongue 22a of second bag 20 so that a complete and continuous weak seal extends between the two bags.

It is preferred that sheet piece 12 of first bag 10 and sheet piece 22 of second bag 20 are aligned with each other in a head-to-tail relationship. Such an arrangement is ensured when second bag weak seal 29 is inserted in and between ears 11a and 13a extending from first bag weak seal 19. Further, ears 11a and 13a of first bag 10 must overlap with at least the end portion of cylindrical sheet 21. Without such an overlapping relationship between those portions, leakage would take place if sheet pieces 12 and 22 are separated away from each other when weak seals 19 and 29 as well as a part of portion 30 are broken in use (see FIG. 5).

In summary, and with reference to FIGS. 3 and 5, the dual-chambered container of the invention has a first chamber 31 and a second chamber 32 for receiving a dry drug and a medical liquid, respectively. These chambers 31 and 32 are formed in the first and second bags 10 and 20, respectively. First bag 10 has a weak seal 19 in a side thereof and second bag 20 has weak seal 29 in a side thereof (see FIG. 3). These weak seals are fusion bonded to one another to isolate the chambers so that liquid cannot pass from one chamber to the other until weak-sealing members 12 and 22 are disjoined from the remainder of the respective seals.

EXAMPLE

In a practical example of the present invention, the rear main sheet for the first bag was made of an aluminum foil laminate (PET/aluminum foil/PE). The weak-sealing member was a small sheet piece made of a polymer blend composed of polyethylene and polypropylene (PE:PP=7:3). The frontal main sheet was made of a PET film with evaporation-deposited silica layers, with this film being sandwiched between PE films (thus represented as "PE/SiO$_2$/PET/SiO$_2$/PE"). The small sheet piece was point welded to the PE layer of the rear sheet. The frontal sheet was overlaid on the rear sheet and their lateral sides were fusion bonded, and a transverse strip about 5 mm wide of the small sheet piece was also fusion bonded to and between the frontal and rear main sheets.

The second bag was made from a cylindrical polyethylene sheet and a small sheet piece of the polymer blend of PE and PP (PE:PP=7:3). The sheet piece protruded about 5 mm from an end of the cylinder so as to form a tongue. The fusion bonding was done across the middle zone of the sheet piece, with the fusion-bonded zone being about 5 mm wide.

The weak seals thus formed to include the tongue did prove easy to open by manually compressing the second bag, without causing any leakage of the medical liquid.

In summary, in the dual-chambered container of the invention the chamber in the first bag for receiving, for example, a dry drug can be effectively sterilized independently of the chamber in the second bag for receiving, for example, a medical liquid. This dispenses with the need for any intricate or special work required for accommodation of the dry drug, thus saving labor and lowering the cost of manufacturing dual-chambered containers, especially those for medical uses.

What is claimed is:

1. A dual-chambered container comprising:
    a first bag having a chamber therein, and having a weak seal formed in an end thereof, said first bag comprising two plastic sheets bonded to one another to form said chamber therein, and said weak seal in said first bag comprising a weak-sealing member sandwiched between said plastic sheets at said end thereof, said weak-sealing member being fusion bonded to said plastic sheets so that portions of said plastic sheets form ears that are not joined to one another and an end of the weak-sealing member is exposed between said ears to form a tongue; and
    a second bag having a chamber therein, and having a weak seal formed in an end thereof and being joined to said first bag, said second bag comprising one of a cylindrical plastic sheet and a pair of plastic sheets having opposing edges bonded to one another to form said chamber therein, and said weak seal in said second bag comprising a weak-sealing member disposed in said end of said second bag, said weak-sealing member being fusion bonded to said end so that a portion of said weak-sealing member protrudes from said end to form a tongue;
    said weak seals in said first and second bags being positioned such that the weak-sealing member of said second bag is inserted in and between the ears of said first bag such that the tongues of said bags are in juxtaposition and the ends of the bags are bonded together such that a complete and continuous weak seal extends between the two bags and forms a passageway when said continuous weak seal is broken,
    wherein said weak-sealing member in each of said first and second bags is a sheet piece of a polymer blend comprised of at least two polymers, one of said polymers comprising the first and second bags and having a limited affinity to the other polymer or polymers in the blend and wherein one chamber contains a dry drug and the other chamber contains a medical liquid.

2. The dual-chambered container of claim 1, wherein the polymer blend comprises polyethylene and polypropylene, the weight ratio of polyethylene to polypropylene being 3:7 to 7:3.

3. The dual-chambered container of claim 2, wherein the first bag is comprised of a rear sheet comprised of a laminate having an outer layer of polyethylene terephthalate, an inner layer of polyethylene, and aluminum foil disposed therebetween, and a frontal sheet comprised of a laminate having an outer layer of one of a copolymer of ethylene and propylene and polyethylene, an inner layer of polyethylene, and a polyethylene terephthalate film coated with a silica layer disposed therebetween.

4. A method of making a dual-chambered containing comprising the steps of:
    forming a first bag having a weak seal in a side thereof by sandwiching a weak-sealing member between plastic sheets and fusion bonding the weak-sealing member to the plastic sheets so that portions of the plastic sheets form ears that are not joined to one another at an end of the first bag, and an end of the weak-sealing member is exposed between said ears to form a tongue;
    forming a second bag having a weak seal in a side thereof by fusion bonding a weak-sealing member to one of a cylindrical plastic sheet and a pair of plastic sheets having opposing edges bonded to one another so that a portion of said weak-sealing member protrudes from an end of the second bag to form a tongue; and
    fusion bonding said sides of said first and second bags so that said weak seals therein are positioned so that a passageway is formed between said first and second bags when said weak seals are forcibly broken,
    wherein the step of fusion bonding the first and second bags includes the steps of inserting the tongue of the second bag between the ears of the first bag so that the tongues of the first and second bags are in juxtaposition, and fusion bonding the ears of the first bag to the tongues of the first and second bags and to the end of the second bag in which the weak-sealing member is disposed; and wherein said weak-seal in each of said first and second bags comprises a weak-sealing member that is a sheet piece of a polymer blend comprised of at least two polymers, one of said polymers comprising the first and second bags and having a limited infinity to the other polymer or polymers in said blend and wherein one chamber contains a dry drug and the other chamber contains a medical liquid.

5. The method of claim 4, wherein the polymer blend comprises polyethylene and polypropylene, the weight ratio of polyethylene to polypropylene being 3:7 to 7:3.

* * * * *